United States Patent [19]
Yoon

[11] Patent Number: 5,591,189
[45] Date of Patent: *Jan. 7, 1997

[54] SAFETY PENETRATING INSTRUMENT WITH SAFETY MEMBER MOVING DURING PENETRATION AND TRIGGERED SAFETY MEMBER PROTRUSION

[76] Inventor: InBae Yoon, 2101 Highland Ridge Dr., Phoenix, Md. 21131

[*] Notice: The term of this patent shall not extend beyond the expiration date of Pat. No. 5,431,635.

[21] Appl. No.: 301,897

[22] Filed: Sep. 7, 1994

Related U.S. Application Data

[63] Continuation-in-part of Ser. No. 83,220, Jun. 24, 1993, Pat. No. 5,431,635, Ser. No. 83,728, Jun. 29, 1993, Pat. No. 5,466,224, and Ser. No. 115,152, Sep. 2, 1993.

[51] Int. Cl.$^6$ ........................................ A61M 5/00
[52] U.S. Cl. .................. 606/185; 604/165; 604/170
[58] Field of Search ............................ 128/751, 752, 128/753, 754; 604/95, 158, 162, 163, 164, 165, 170, 272, 274, 280, 169; 606/167, 171, 185

[56] References Cited

U.S. PATENT DOCUMENTS

| | | | |
|---|---|---|---|
| 5,158,552 | 10/1992 | Borgia et al. | 604/165 |
| 5,312,354 | 5/1994 | Allen et al. | 604/157 |
| 5,431,635 | 7/1995 | Yoon | 604/165 |

Primary Examiner—Guy V. Tucker

[57] ABSTRACT

A safety penetrating instrument for penetrating an anatomical cavity wall to gain access to an anatomical cavity includes a penetrating member having a distal end for penetrating the anatomical cavity wall, a distally-biased safety member having a distal end movable between an extended position where the safety member distal end protrudes distally from the penetrating member distal end to protect the distal end of the penetrating member and a retracted position where the safety member distal end is disposed proximally of the penetrating member distal end to expose the penetrating member distal end, an extending mechanism for moving the safety member to the extended position and for permitting the safety member to move proximally toward the retracted position, a handle for manually moving the safety member proximally to the retracted position and a lock for locking the safety member in the retracted position to prevent movement of the safety member to the extended position during penetration of the anatomical cavity wall. The safety member can be one or both of a cannula and a safety shield or probe with the safety shield or probe being movable proximally from the retracted position during penetration of the anatomical cavity wall and distally toward the retracted position in response to introduction in the anatomical cavity. The safety penetrating instrument is responsive to movement of the safety shield or probe distally to trigger release of the lock to permit the extending mechanism to move the safety member to the extended position.

27 Claims, 6 Drawing Sheets

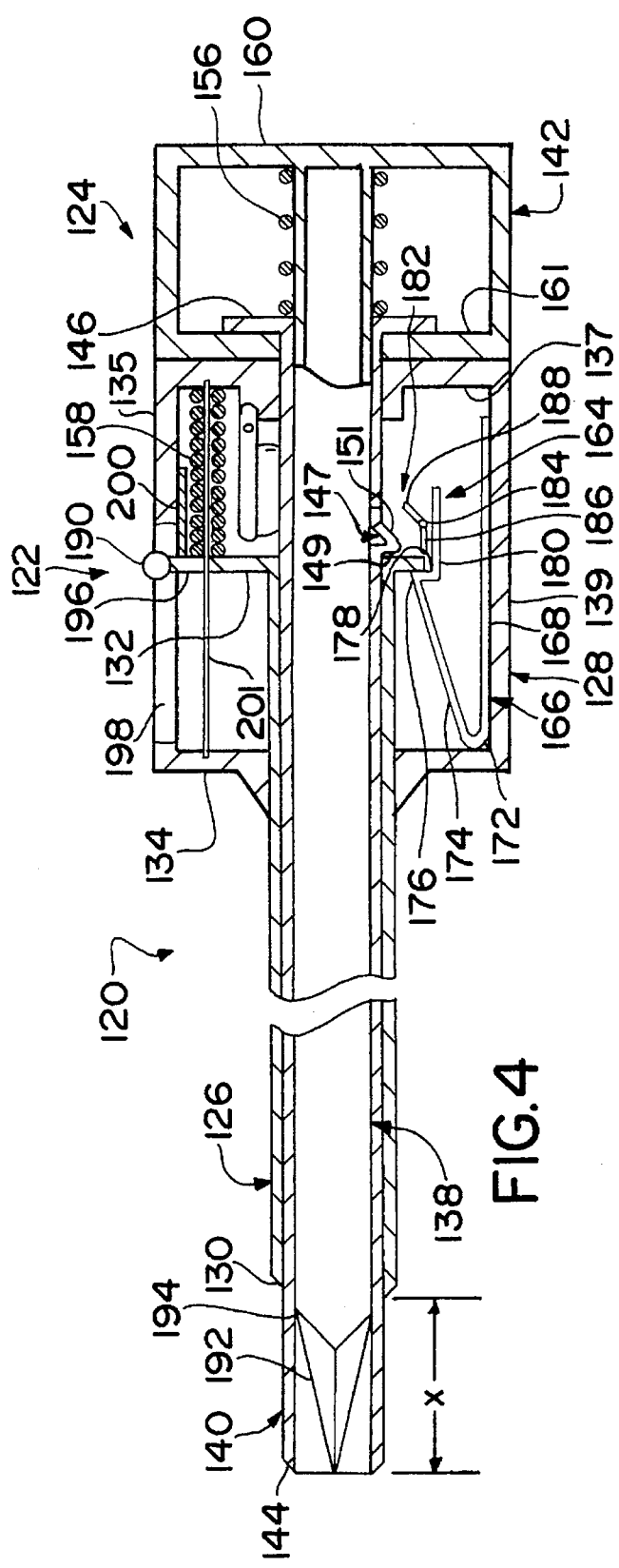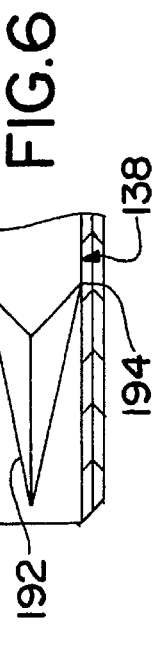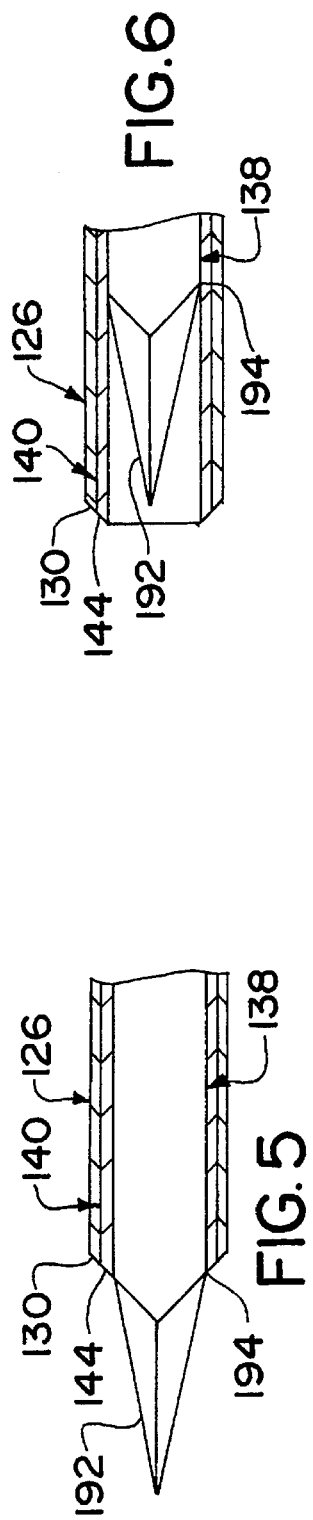

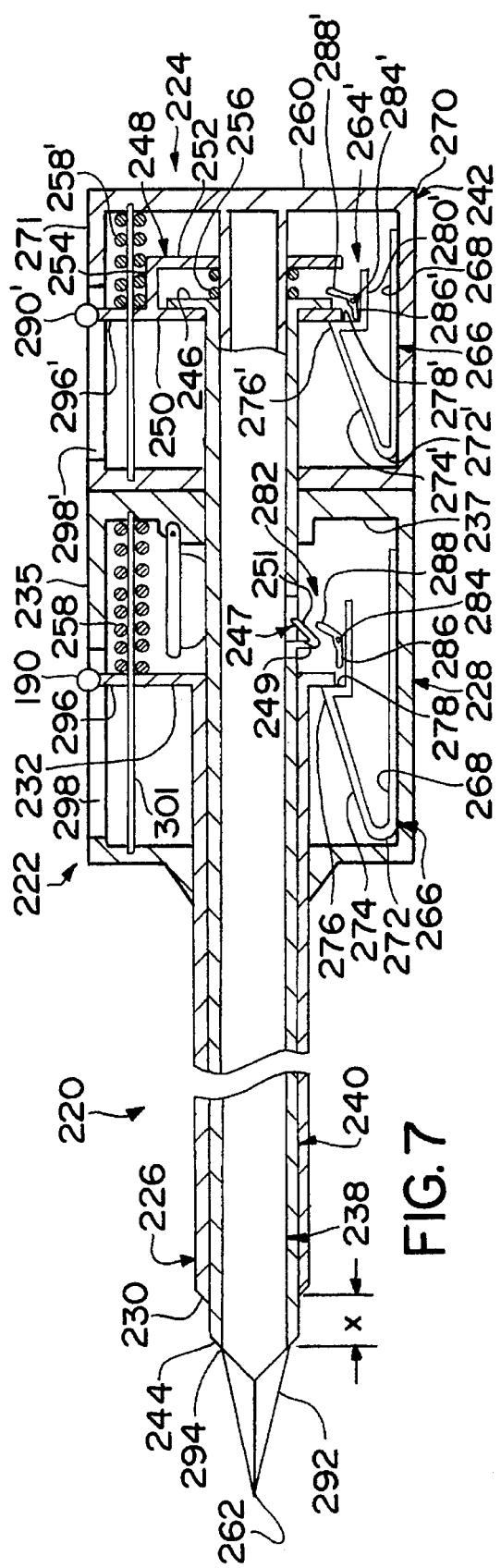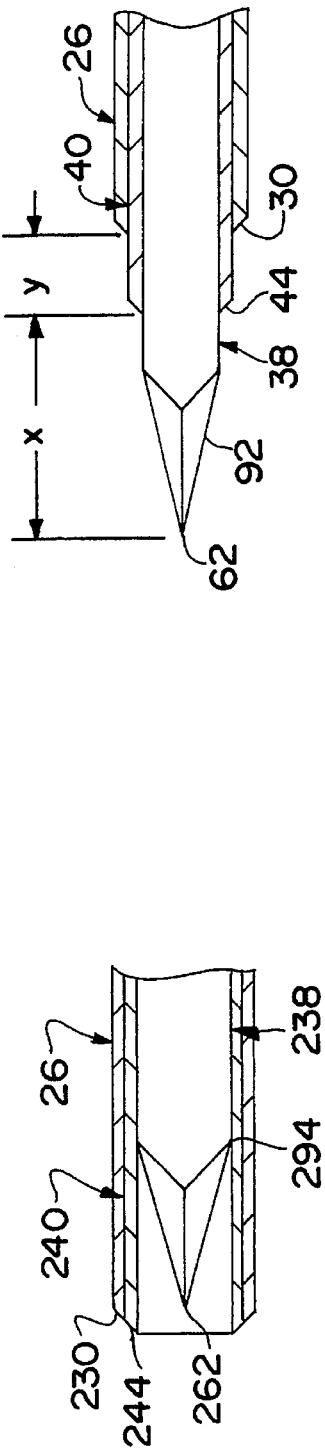

SAFETY PENETRATING INSTRUMENT WITH SAFETY MEMBER MOVING DURING PENETRATION AND TRIGGERED SAFETY MEMBER PROTRUSION

CROSS-REFERENCE TO RELATED APPLICATIONS

This application is a continuation-in-part of prior applications Ser. No. 08/083,220, filed Jun. 24, 1993, now U.S. Pat. No. 5,431,635, Ser. No. 08/083,728, filed Jun. 29, 1993, now U.S. Pat. NO. 5,466,224, and Ser. No. 08/115,152, filed Sep. 2, 1993, still pending, the disclosures of which are incorporated herein by reference.

BACKGROUND OF THE INVENTION

1. Field of the Invention

The present invention pertains to safety penetrating instruments and, more particularly, to safety penetrating instruments for use in forming portals for establishing communication with anatomical cavities wherein tissue and organ structures are protected from the tips of the penetrating members and to methods of penetrating anatomical cavity walls with safety penetrating instruments.

2. Discussion of the Prior Art

Penetrating instruments are widely used in medical procedures to gain access to anatomical cavities ranging in size from the abdomen to small blood vessels, such as veins and arteries, epidural, pleural and subarachnoid spaces, heart ventricles and spinal and synovial cavities. Use of penetrating instruments has become an extremely popular and important first step in endoscopic, or minimally invasive, surgery to establish an endoscopic portal for many various procedures, such as laparoscopic procedures in the abdominal cavity. Such penetrating instruments typically include a cannula or portal sleeve and a penetrating member disposed within the cannula and having a sharp tip for penetrating an anatomical cavity wall with the force required to penetrate the cavity wall being dependent upon the type and thickness of the tissue forming the cavity wall. Once the wall is penetrated, it is desirable to protect the sharp tip of the penetrating member from inadvertent contact with or injury to tissue or organ structures in or forming the cavity in that, once penetration is achieved, the lack of tissue resistance can result in the sharp tip traveling too far into the cavity and injuring adjacent tissue or organ structures.

Various safety penetrating instruments have been proposed, generally falling into protruding and retracting categories. In protruding safety penetrating instruments, a safety member is spring biased to protrude beyond the tip of the penetrating member in response to the reduced force on the distal end of the safety member upon entry into the anatomical cavity. The safety member can be disposed around the penetrating member in which case the safety member is frequently referred to as a shield, or the safety member can be disposed within the penetrating member in which case the safety member is frequently referred to as a probe. In retracting safety penetrating instruments, the penetrating member is retracted into the cannula upon entry into the anatomical cavity in response to distal movement of a component of the safety penetrating instrument such as the penetrating member, the cannula, a probe or a safety member such as a shield or probe.

While protruding safety penetrating instruments have been well received, there is room for improvement in reducing the force required to penetrate the cavity wall which necessarily includes the force required to overcome the spring bias on the safety member as well as the resistance of the cavity wall and insuring that the safety member protrudes which normally requires increasing the spring bias on the safety member and, thus, the force to penetrate. Retracting safety penetrating instruments have the disadvantages of requiring relatively complex mechanisms to hold the penetrating member in an extended position during penetration and to release the penetrating member for retraction and, concomitantly, not retracting sufficiently quickly and reliably.

SUMMARY OF THE INVENTION

Accordingly, it is a primary object of the present invention to improve safety penetrating instruments of the type having a penetrating member and a safety member biased distally to protrude beyond the distal end of the penetrating member by easing penetration and assuring protrusion of the safety member.

Another object of the present invention is to reduce the force-to-penetrate required to penetrate an anatomical cavity wall with a safety penetrating instrument of the type having a distally-biased safety member for protruding beyond a distal end of a penetrating member once penetration into the cavity has been achieved.

A further object of the present invention is to increase the force biasing a safety member distally in a safety penetrating instrument to assure protrusion of the safety member after penetration into an anatomical cavity without increasing the force-to-penetrate required for penetration.

The present invention has an additional object to use a cannula of a safety penetrating instrument as a safety member and to trigger movement of the cannula to an extended position protruding beyond a penetrating member distal end in response to distally-biased movement of a safety shield or probe upon penetrating into an anatomical cavity.

Another object of the present invention is to use a safety shield or probe as a safety member in a safety penetrating instrument and to trigger movement of the safety shield or probe to an extended position protruding beyond a penetrating member distal end in response to distally-biased movement of the safety shield or probe upon penetrating into an anatomical cavity.

Yet another object of the present invention is to use both a cannula and a safety shield or probe as safety members in a safety penetrating instrument and to trigger movement of the safety members to extended positions protruding beyond a penetrating member distal end in response to distally-biased movement of the safety shield or probe upon penetrating into an anatomical cavity.

Some of the advantages of the safety penetrating instrument of the present invention are that the distal extending force on a safety member can be designed to assure protrusion of the safety member upon penetration regardless of the anatomical cavity being penetrated, that the force-to-penetrate of a safety penetrating instrument can be minimized to permit use in delicate tissue, that release of the safety member for movement to the extended protruding position can be triggered by distally-biased movement of a safety shield or probe in response to penetration through the tissue, and that the safety penetrating instrument can be inexpensively manufactured with minimum components to reduce cost, facilitate sterilization for re-use and allow economical single-patient use.

The present invention is generally characterized in a safety penetrating instrument including a penetrating member having a distal end for penetrating an anatomical cavity wall to gain access to an anatomical cavity, a safety member having a distal end movable between an extended position where the safety member distal end is disposed distally of the penetrating member distal end to protect the penetrating member distal end and a retracted position where the safety member distal end is disposed proximally of the penetrating member distal end to expose the penetrating member distal end, extending means for moving the safety member distally to the extended position and for permitting the safety member to move proximally to the retracted position, means for manually moving the safety member proximally from the extended position to the retracted position and locking means for locking the safety member in the retracted position to prevent movement of the safety member to the extended position prior to penetration of the anatomical cavity wall. The safety member can be a safety shield or probe biased distally in the retracted position to be movable proximally from the retracted position during penetration of the anatomical cavity wall by the safety penetrating instrument and distally toward the retracted position upon penetration into the anatomical cavity by the safety penetrating instrument, or a cannula, or both a cannula and a safety shield or probe. Releasing means responsive to distally-biased movement of the safety shield or probe upon penetration into the anatomical cavity triggers release of the locking means to permit the extending means to move the safety member to the extended position.

Other objects and advantages of the present invention will become apparent from the following description of the preferred embodiments taken in conjunction with the accompanying drawings wherein, unless specified otherwise, like parts or parts that perform like functions are identified in each of the several figures by the same reference character or by reference characters sharing the same last two digits.

BRIEF DESCRIPTION OF THE DRAWINGS

FIG. 4 is a broken side view, partly in section, of a modification of a safety penetrating instrument according to the present invention.

FIG. 5 is a side view, partly in section, of the distal end of the safety penetrating instrument of FIG. 4 during penetration of a wall of an anatomical cavity.

FIG. 6 is a side view, partly in section, of the distal end of the safety penetrating instrument of FIG. 4 following penetration into the anatomical cavity.

FIG. 7 is a broken side view, partly in section, of a further modification of a safety penetrating instrument according to the present invention.

FIG. 8 is a side view, partly in section, of the distal end of the safety penetrating instrument of FIG. 7 following penetration through an anatomical cavity wall.

FIG. 9 is a side view, partly in section, of an alternative distal configuration for the safety penetrating instrument of the present invention.

DESCRIPTION OF THE PREFERRED EMBODIMENTS

The safety penetrating instrument of the present invention is described hereinafter for use as an instrument for inserting a portal sleeve through a wall of an anatomical cavity to form a portal for the introduction of various surgical and diagnostic instruments into the cavity during endoscopic procedures, such as laparoscopy. It is understood, however, that the safety penetrating instrument of the present invention can be used for safe penetration or introduction into anatomical cavities of needles with fluid flow therethrough and catheters as well as for other instruments engaging tissue during surgical or diagnostic procedures. Accordingly, the cannula or outer tubular member of the safety penetrating instrument can be a portal sleeve, a needle, a catheter or a tubular component of a medical instrument.

Figure 1:
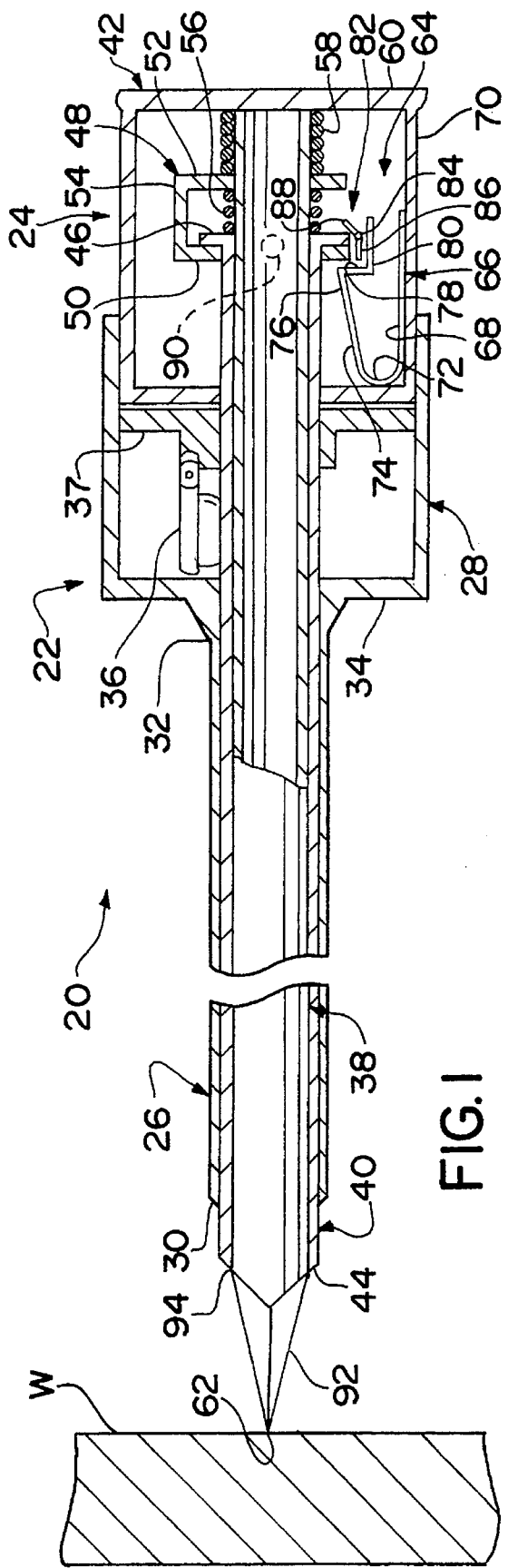
FIG. 1 is a broken side view, partly in section, of a safety penetrating instrument according to the present invention.

A safety penetrating instrument 20 according to the present invention, as shown in FIG. 1, includes a portal unit 22 and a penetrating unit 24. The portal unit 22 can be made of any desirable, medical grade materials depending on procedural use and desirability of being for single patient use or re-usable. The portal unit 22 includes an elongate portal sleeve, cannula or catheter 26 and a housing 28 mounting a proximal end of portal sleeve 26. Portal sleeve 26 terminates distally at a distal end 30 and proximally at a proximal end 32 secured to front wall 34 of housing 28. Portal sleeve 26 can have any desirable cross-sectional configuration, including cylindrical or tubular configurations, in accordance with the procedure to be performed and the anatomical cavity to be penetrated. Preferably, portal sleeve 26 is made of a substantially cylindrical length of rigid or flexible and transparent or opaque material, such as stainless steel or other medically acceptable plastic or metal material, and has a tubular configuration defining a lumen between the distal and proximal portal sleeve ends for receiving a penetrating member 38 of penetrating unit 24.

Housing 28 can be made of any desirable material and can have any desirable configuration to facilitate grasping by a surgeon and includes a rear wall 37 having an opening therein aligned with an opening in the housing front wall 34 to allow passage therethrough by the penetrating member 38. The housing 28 is preferably constructed to sealingly engage instruments passing therethrough and to include a valve biased to a closed state when no instrument passes through the portal sleeve. A flapper valve 36 is shown; however, any suitable valve construction can be utilized, including trumpet or nipple valves.

Penetrating unit 24 includes penetrating member 38, safety shield 40 and hub 42 mounting proximal ends of the penetrating member and the safety shield. Housing 28 defines a rearward-facing recess configured for receiving hub 42; and when the hub is mated with the housing as shown, safety shield 40 is disposed between penetrating member 38 and portal sleeve 26. The safety shield terminates distally at a distal end 44 and proximally at a transverse flange 46 disposed between walls of a rail member 48 mounted in hub 42. Rail member 48 is disposed in hub 42 and is generally U-shaped including a forward wall 50 disposed transverse or perpendicular to a longitudinal axis of the penetrating instrument, a rearward wall 52 in configuration parallel to forward wall 50 and a side wall 54 transversely joining the forward and rearward rail member walls. Flange 46 is disposed between the rail member forward and rearward walls with the rail member forward wall 50 having an opening therein allowing passage therethrough by the safety shield 40. The rail member forward and rearward walls are disposed parallel or substantially parallel to flange 46, and a bias member 56 is connected between safety shield flange 46 and the rail member rearward wall 52 to bias the safety shield distally. As shown, bias member 56 includes a helical coil spring disposed around the penetrating member 38 and mounted in compression between flange 46 and the rail member rearward wall 52 to bias the safety shield 40 distally to cause flange 46 to abut the rail member forward wall 50. However, bias member 56 can include various other types of springs as well as other types of bias devices including compression springs, tension springs, torsion springs, pan springs, leaf springs, rubber, plastic or magnets, for example. An extending member 58 is mounted between rail member rearward wall 52 and a rear wall 60 of hub 42 to bias the safety shield 40 in a distal direction to an extended protruding position where distal end 44 of the safety shield is disposed beyond a sharp tip of the penetrating member 38 as will be explained further below. The extending member includes a helical coil spring disposed around the penetrating member 38 and mounted in compression between the rail member rearward wall 52 and the hub rearward wall 60 to bias the rail member 48 and, therefore, the safety shield 40, in a distal direction to an extended protruding position where the distal end 44 of the safety shield is disposed beyond the sharp tip 62 of the penetrating member.

A locking and releasing mechanism 64 for locking the safety shield in a retracted position, shown in FIG. 1, exposing the sharp distal tip 62 of the penetrating member and for releasing the rail member 48 to allow the safety shield 40 to move to the extended protruding position includes a latch or locking spring 66, made of a strip of resilient material, formed to have a substantially flat base 68 secured to a bottom wall 70 of hub 42 and a bend 72 joining the base 68 with an upwardly angled arm 74 spaced from the base. Arm 74 carries or forms a latch 76 having a distal angled latching surface joining a proximal latching surface 78 disposed substantially transverse to the longitudinal axis of the safety penetrating instrument and substantially parallel to the rail member forward wall 50. Arm 74 has an extension 80 positioned proximally of latch 76, and a releasing member or trigger 82 is juxtaposed with extension 80. The trigger 82 is pivotally mounted in the hub on a pin 84 secured to a wall or walls of the hub or structure supported in the hub, and the trigger is generally L-shaped with a leg 86 overlying extension 80 and a leg 88 extending transversely from leg 86 but at a slight angle toward the proximal end of the safety penetrating instrument. A torsion spring (not shown) is coiled around pin 84 and fixed to trigger 82 to bias the trigger counterclockwise, looking at FIG. 1, such that leg 86 is biased toward extension 80.

A handle 90 can be coupled with the safety shield 40, such as with flange 46 or rail member 48, for movement along a slot formed in hub 42 to move the safety shield from the extended protruding position to the locked retracted position as previously explained above.

Penetrating member 38 has a distal end 92 extending from a transverse dimensional transition 94 to distal tip 62 and a proximal end secured to rear wall 60 of hub 42. The portal unit 22 and the penetrating unit 24 can be provided separately or assembled together as shown in FIG. 1, and either or both of the portal and penetrating units can be manufactured in a manner to be disposable for single patient use or to be sterilizable for re-use. The hub 42 can be coupled to the housing 28 by suitable detent or latch mechanisms if desired, and the penetrating unit can be withdrawn from the portal unit leaving the portal sleeve 26 in place within an anatomical cavity to serve as a portal for the introduction of medical instruments therethrough.

Figure 3:
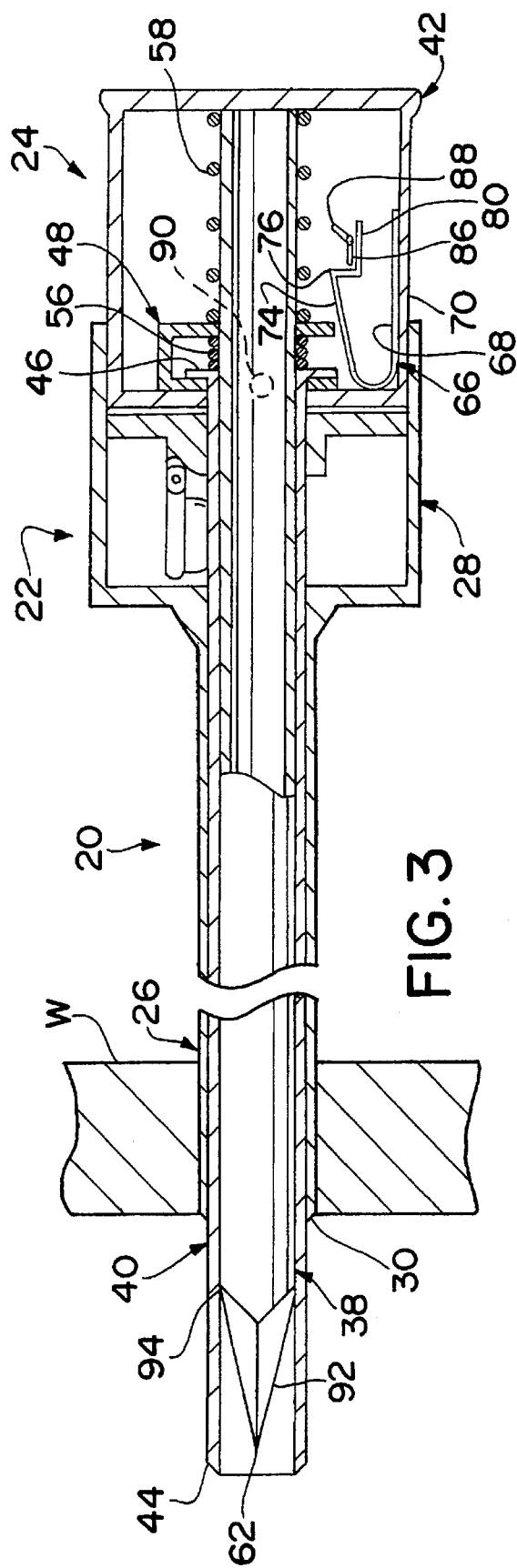
FIG. 3 is a broken side view, partly in section, of the safety penetrating instrument of FIG. 1 following penetration into the anatomical cavity.

In use, the safety shield 40 of safety penetrating instrument 20 will initially be in the extended protruding position shown in FIG. 3 with the safety shield distal end 44 disposed beyond the distal end 92 of penetrating member 38 to protect the sharp tip 62 of the penetrating member. In order to move the safety shield to the retracted position shown in FIG. 1, the handle 90 is grasped to move the safety shield proximally until the rail member forward wall 50 rides over latch 76 to be latched in the retracted position with the rail member forward wall 50 locked against proximal latching surface 78. The user can feel the rail member forward wall 50 lock into place in engagement with the latch 76 and can also visually determine that the safety shield is in the locked retracted position by noting the position of the handle 90 at a proximal end of the slot.

With the safety shield 40 in the locked retracted position illustrated in FIG. 1, the distal end 44 of the safety shield 40 will be disposed proximally of the distal tip 62 of the penetrating member in alignment with the transverse dimensional transition 94. Penetration of the cavity wall W is commenced, and the force from tissue contact on the distal end 44 of the safety shield 40 will cause the safety shield to move proximally against the bias of bias member 56 causing flange 46 to move past trigger leg 88. Movement of flange 46 proximally past trigger leg 88 does not cause movement of latch 76 since there is no contact of trigger leg 86 with arm extension 80; and, accordingly, flange 46 is now positioned proximally of trigger leg 88 as shown in FIG. 2.

Figure 2:
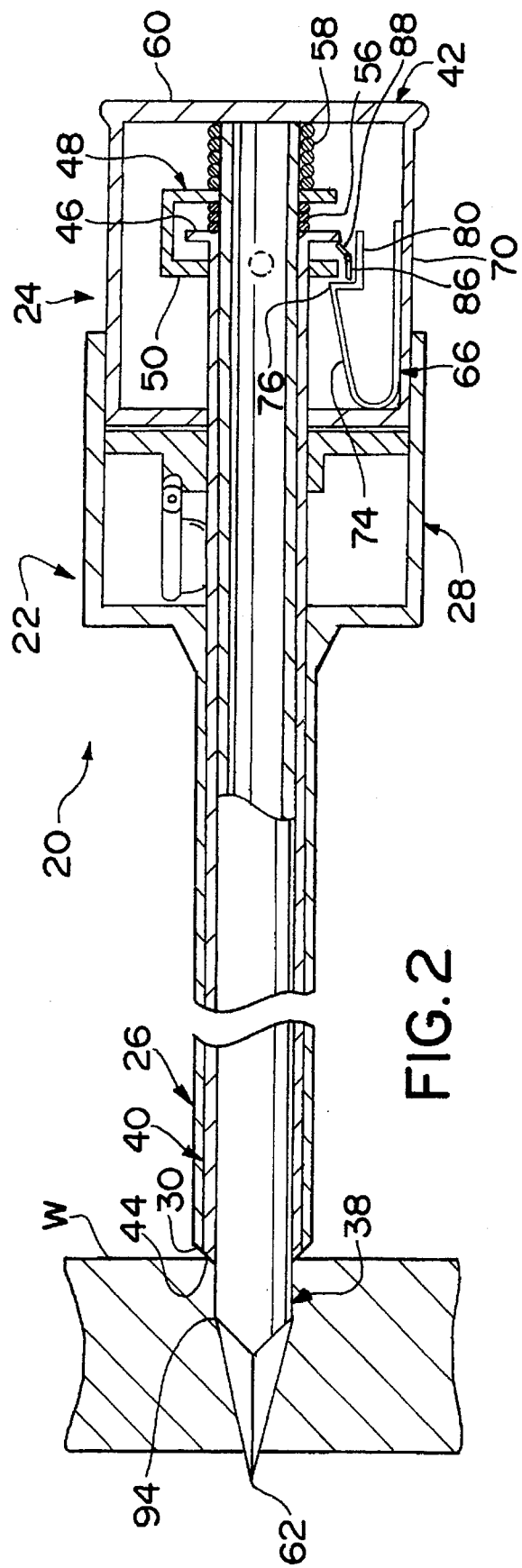
FIG. 2 is a broken side view, partly in section, of the safety penetrating instrument of FIG. 1 during penetration of a wall of an anatomical cavity.

Upon entry into the anatomical cavity, the counter force on the distal end of the safety shield caused by tissue contact will be reduced allowing bias member 56 to move the safety shield distally causing flange 46 to engage trigger leg 88 and pivot the trigger counterclockwise looking at FIG. 2 causing leg 86 to engage arm extension 80. The engagement of leg 86 with arm extension 80 causes arm 74 to move toward base 68 moving the latch 76 out of engagement with the rail member forward wall 50 thereby allowing spring 58 to cause the safety shield to move further distally to the extended protruding position wherein safety shield distal end 44 protrudes beyond the distal end 92 of the penetrating member as shown in FIG. 3. The penetrating unit 24 including the penetrating member 38 and the safety shield 40 can then be withdrawn from the portal unit 22 leaving the portal sleeve 26 in place to serve as a portal for introducing medical instruments therethrough.

A modification of the safety penetrating instrument of the present invention is shown in FIG. 4 at 120. The modified safety penetrating instrument 120 is similar to safety penetrating instrument 20 except that the safety member for safety penetrating instrument 120 includes the cannula, and movement of the cannula to the extended protruding position is triggered by movement of the safety shield in response to a reduction in the force from tissue contact following entry into the anatomical cavity. Safety penetrating instrument 120 includes a portal unit 122 and a penetrating unit 124, the penetrating unit 124 being similar to penetrating unit 24 inasmuch as it includes a penetrating member 138, a safety shield 140 and a hub 142 mounting proximal ends of the penetrating member and safety shield. Safety shield 140 is similar to safety shield 40 and terminates distally at a distal end 144 and proximally at a transverse flange or plate 146 disposed in hub 142. A bias member 156 in the form of a helical coil spring is disposed around the penetrating member 138 and held in compression between the safety shield flange 146 and the rear wall 160 of the hub 142 to bias the safety shield 140 distally and to cause flange 146 to abut the forward wall of the hub 142. Like bias member 56, the bias member 156 for safety penetrating instrument 120 can include various other types of springs as well as other types of bias devices including compression springs, tension springs, torsion springs, pan springs, leaf springs, rubber, plastic or magnets, for example.

The safety shield 140 is generally tubular and can be formed of any suitable material to have a hollow configuration conforming to the configuration of the penetrating member 138. The safety shield 140 further includes a tab or protrusion 147 formed intermediate the safety shield proximal and distal ends so as to be located within the housing 128 of portal unit 122 when hub 142 is mated with the rear of housing 128. The protrusion 147 can be a separate member carried by the safety shield 140 or integrally formed as a part of the safety shield, for example from a tongue of material cut from the safety shield 140 and configured as shown to present a distally facing abutment surface 149 oriented perpendicular to the longitudinal axis of the safety shield and a tapered proximal surface 151.

Penetrating member 138 is coaxially disposed within safety shield 140 and includes a proximal end fixed to the rear wall 160 of hub 142 and a distal end 192 extending from a transverse dimensional transition 194. Safety shield distal end 144 is spaced distally of the transverse dimensional transition 194 a predetermined distance X corresponding approximately to the spacing between the safety shield flange 146 and the rear wall 160 of the hub when bias member 156 is fully extended in the rest position shown.

Portal unit 122 is similar to portal unit 22 and includes a portal sleeve 126 and housing 128 mounting the proximal end of the portal sleeve. Portal sleeve 126 terminates distally at a distal end 130 and proximally at a transverse flange 132 disposed in housing 128 with the portal sleeve passing through an opening in a front wall 134 of the housing. The portal sleeve 126 can have any desirable cross-sectional configuration, including cylindrical or tubular configurations, in accordance with the procedure to be performed and the anatomical cavity to be penetrated. Preferably, portal sleeve 126 is made of a substantially cylindrical length of rigid or flexible and transparent or opaque material, such as stainless steel or other medically acceptable plastic or metal material, and has a tubular configuration defining a lumen between the distal and proximal portal sleeve ends for receiving the penetrating member 138 of penetrating unit 124.

Portal sleeve flange 132 extends toward the upper wall 135 of housing 128, and a pin 196 extends from flange 132 through a slot 198 in the housing upper wall 135 to terminate at a handle or knob 190 positioned at or near the proximal end of the slot 198. Slot 198 extends longitudinally in parallel with the longitudinal axis of the safety penetrating instrument 120, and an indicator strip 200 extends proximally from flange 132 to be visible through and along the length of slot 198 when the portal sleeve is in the extended protruding position as will be described further below. The indicator strip 200 can be colored and/or can be provided with any desirable indicia, and the slot 198 can be provided with a transparent window or cover for viewing of the indicator strip therethrough. An extending member 158 is mounted between the portal sleeve flange 132 and the rear wall 137 of housing 128 to bias the portal sleeve 126 in a distal direction toward an extended protruding position where the distal end 130 of the portal sleeve is disposed beyond the penetrating member distal end 192. The extending member 158 can include a helical coil spring mounted in compression between the portal sleeve flange 132 and the housing rear wall 137 as shown, or the extending member can include any other type of spring or other bias device as discussed for bias member 156. If desired, a guide rod 201 can be connected between the front wall 134 and the rear wall 137 of housing 128 with the spring 158 disposed around the guide rod.

A locking and releasing mechanism 164 for locking the portal sleeve in the retracted position, shown in FIG. 1, exposing the sharp distal end of the penetrating member and for releasing the portal sleeve to allow the portal sleeve to move to the extended protruding position includes a latch or locking spring 166, made of a strip of resilient material, formed to have a substantially flat base 168 secured to a bottom wall 139 of housing 128 and a bend 172 joining the base 168 with an upwardly angled arm 174 spaced from the base. Arm 174 carries or forms a latch 176 having a distal angled latching surface joining a proximal latching surface 178 disposed substantially transverse to the longitudinal axis of the safety penetrating instrument and substantially parallel to the portal sleeve flange 132. Arm 174 has an extension 180 positioned proximally of latch 176, and a releasing member or trigger 182 is juxtaposed with extension 180. The trigger 182 is pivotally mounted in the housing on a pin 184 secured to a wall or walls of the housing or a structure supported in the housing, and the trigger is generally L-shaped with a leg 186 overlying extension 180 and a leg 188 extending transversely from leg 186 but at a slight angle toward the proximal end of the safety penetrating instrument. A torsion spring (not shown) is coiled around pin 184 and fixed to trigger 182 to bias the trigger counterclockwise, looking at FIG. 4, such that leg 186 is biased toward extension 180. When portal sleeve flange 132 is engaged by latch 176, portal sleeve distal end 130 is aligned with the transverse dimensional transition 194 of the penetrating member 138.

Use of the safety penetrating instrument 120 is similar to that described above with respect to safety penetrating instrument 20 in that, when the user desires to penetrate into an anatomical cavity, the safety penetrating instrument will normally be provided with the safety shield 140 in the extended position where the distal end 144 of the safety shield protrudes beyond the penetrating member distal end 192. Additionally, the portal sleeve 126 will be provided in the extended protruding position shown in FIG. 6, where the distal end 130 of the portal sleeve protrudes beyond the penetrating member distal end 192. The portal sleeve 126 will be biased to the extended protruding position by extending member 158 such that handle 190 will be disposed at a distal end of slot 198 with portal sleeve flange 132 disposed distally of latch 176. The safety shield 140 will be biased distally by bias member 156 with safety shield flange 144 being biased into abutment with hub front wall 161.

Prior to commencing penetration of an anatomical cavity wall, handle 190 is grasped and manually moved proximally to move portal sleeve 126 proximally against the bias of extending member 158 until portal sleeve flange 132 rides over latch 176 by engaging upwardly angled arm 174 to move the arm 174 toward the base 168. The portal sleeve 126 will then be locked in the retracted position due to engagement of portal sleeve flange 132 with proximal latching surface 178 as shown in FIG. 4. The user can feel the portal sleeve flange lock into place in engagement with latch 176 and can also visually determine that the portal sleeve is in the locked retracted position by noting the position of the handle 190 at a proximal end of slot 198 at which time indicator strip 200 will no longer be visible or will be only slightly visible along the slot. With the portal sleeve 126 locked in the retracted position, the distal end 130 of the portal sleeve will be disposed adjacent to the transverse dimensional transition 194 of the penetrating member 138, the distal end 144 of the safety shield 140 will be disposed distally of the sharp tip 162 of the penetrating member, and safety shield flange 144 will remain biased by spring 156 into abutment with hub forward wall 161.

With the safety penetrating instrument 120 in the position illustrated in FIG. 4, penetration of the anatomical cavity wall is commenced, and the force from tissue contact on the distal end 144 of the safety shield 140 will cause the safety shield to move proximally against the bias of spring 156 towards being in alignment with the portal sleeve distal end 130 and the transverse dimensional transition 194 as shown in FIG. 5. Proximal movement of the safety shield 140 also causes the protrusion 147 carried by the safety shield to move past trigger leg 188 without causing movement of latch 176; and, accordingly, the protrusion 147 will then be positioned proximally of the trigger 182. Upon entry into the anatomical cavity, the counter force on the distal end of the safety shield will be reduced allowing spring 156 to move the safety shield distally causing protrusion 147 to engage leg 188 of trigger 182 and thereby to pivot the trigger counterclockwise causing leg 186 to engage arm extension 180. The engagement of leg 186 with extension 180 causes arm 174 to move toward base 168 moving the latch 176 out of engagement with portal sleeve flange 132 thereby allowing spring 158 to cause the portal sleeve to move distally to the extended protruding position shown in FIG. 6 wherein the portal sleeve distal end 130 protrudes beyond the distal end 192 of penetrating member 138. The penetrating unit 124 can then be withdrawn from the portal unit 122 leaving the portal sleeve 126 in place for the introduction of medical instruments therethrough.

Another modification of a safety penetrating instrument according to the present invention is shown in FIG. 7 at 220 and is similar to safety penetrating instrument 120 with the exception that the safety shield proximal end is mounted by a rail member lockable in a retracted position against the influence of an extending member so that both the portal sleeve and safety shield are triggered to move to extended protruding positions to serve as safety members upon penetration of the safety shield into the anatomical cavity. Safety penetrating instrument 220 includes a portal unit 222 and a penetrating unit 224. Portal unit 222 is similar to portal unit 122 and includes a portal sleeve 226 and a housing 228 mounting the proximal end of the portal sleeve. Portal sleeve 226 is similar to portal sleeve 126 with the exception that portal sleeve distal end 230 is spaced proximally of the transverse dimensional transition of the penetrating member a distance X when retracted. Portal sleeve 226 terminates proximally at flange 232 disposed in housing 228 and extending transversely toward the top wall 235 of the housing with a pin 296 extending from portal sleeve flange 232 through slot 298 in the housing upper wall to terminate at a handle or knob 290. An extending member 258 in the form of a helical coil spring is held in compression between the portal sleeve flange 232 and the rear wall 237 of the housing to bias the portal sleeve 226 in a distal direction toward an extended protruding position shown in FIG. 8.

Locking and releasing mechanism 264 is the same as mechanism 164 for safety penetrating instrument 120 with the latch being made of a strip of resilient material formed to have a substantially flat base 268 secured to a bottom wall of housing 228 and a bend 272 joining the base 268 with an arm 274 disposed parallel or substantially parallel with a longitudinal axis of the safety penetrating instrument 220 and with base 268. Arm 274 carries latch 276 which has a distal angled latching surface joining a proximal latching surface 278 disposed substantially transverse to the longitudinal axis of the safety penetrating instrument and substantially parallel to portal sleeve flange 232. Trigger 282 is juxtaposed with arm 274 to be disposed distally of latch 276 and is similar to trigger 182 with a leg 286 overlying arm 274 and a leg 288 extending substantially transversely from leg 286 but at a slight angle toward the proximal end of the safety penetrating instrument.

Penetrating unit 224 is similar to penetrating unit 24 for safety penetrating instrument 20 and includes a penetrating member 238, a safety shield 240 and a hub 242 mounting proximal ends of the penetrating member and safety shield. Penetrating member 238 includes a proximal end fixed to the rear wall 260 of hub 242 and a distal end 292 extending from a transverse dimensional transition 94 to terminate at tip 262. Safety shield 240 is similar to safety shield 140 in that it carries a radially extending protrusion 247 having a transverse distal face 249 and an angled proximal face 251 for engaging trigger 282 mounted in housing 228. Safety shield 240 terminates distally at a distal end 244 and proximally at a transverse flange 246 mounted by a rail member 248 disposed in hub 242. Rail member 248 is generally U-shaped including a forward wall 250 disposed transverse or perpendicularly to a longitudinal axis of the penetrating instrument, a rearward wall 252 in configuration parallel to forward wall 250 and a sidewall 254 transversely joining the forward and rearward rail member walls. Flange 246 is disposed between the rail member forward and rearward walls with the rail member forward wall 250 having an opening therein allowing passage therethrough by the safety shield 240. The rail member forward and rearward walls are disposed parallel or substantially parallel to flange 246, and a bias member 256 is connected between flange 246 and the rail member rearward wall 252 to bias the safety shield distally. As shown, bias member 256 includes a helical coil spring held in compression between flange 246 and the rail member rearward wall 252 to bias the safety shield 240 distally to cause flange 246 to abut the rail member forward wall 250. Bias member 256 can include any of the other types of springs or bias devices previously described in connection with bias members 56 and 156. Rail member rearward wall 252 extends toward an upper wall 271 of hub 242, and an extending member 258' is mounted between rail member rearward wall 252 and a rear wall 260 of hub 242 to bias the safety shield 240 in a distal direction to an extended protruding position where the distal end 244 of the safety shield is disposed beyond the sharp tip 262 of penetrating member 238 as shown in FIG. 8. Like extending member 58 for safety penetrating instrument 20, extending member 258' can include a helical coil spring mounted in compression between rail member rearward wall 252 and the hub rear wall 260 around penetrating member 238. A pin 296' extends from rail member forward wall 250 through a slot 298' formed in hub upper wall 271 to terminate at a handle or knob 290'.

A locking and releasing mechanism 264' for safety shield 240 is similar to locking and releasing mechanism 264 for portal sleeve 226 but is disposed within the hub 242. The locking and releasing mechanism 264 locks the safety shield 240 in a retracted position, shown in FIG. 7, exposing the sharp distal end of the penetrating member and also releases the safety shield 240 to allow the safety shield to move to the extended protruding position shown in FIG. 8. Locking and releasing mechanism 264' includes a latch or locking spring 266', made of a strip of resilient material, and formed to have a substantially flat base 268' secured to a bottom wall 270 of hub 242 and a bend 272' joining the base 268' with an upwardly angled arm 274' spaced from the base. Arm 274' carries or forms a latch 276' having a distal angled latching surface joining a proximal latching surface 278' disposed substantially transverse to the longitudinal axis of the safety penetrating instrument and substantially parallel to the rail member forward wall 250. Arm 274' has an extension 280' positioned proximally of latch 276' and a releasing member trigger 282' is juxtaposed with extension 280'. Trigger 282' is pivotally mounted in the hub on a pin 284' secured to a wall or walls of the hub or structure supported in the hub and is generally L-shaped with a leg 286' overlying extension 280' and a leg 288' extending transversely from the leg 286' but at a slight angle.

Use of the safety penetrating instrument 220 is similar to that previously described; however, both the portal sleeve 226 and the safety shield 240 will initially be in the extended protruding positions shown in FIG. 8 with the portal sleeve distal end 230 and the safety shield distal end 244 being disposed beyond the distal end 292 of penetrating member 238 to protect the sharp tip of the penetrating member. In order to move the portal sleeve and safety shield to the retracted positions shown in FIG. 7, handles 290 and 290' are grasped one at a time or simultaneously to move the portal sleeve and safety shield proximally until the safety shield rail member forward wall 250 rides over latch 276' to be latched in the retracted position with the rail member forward wall 250 locked against proximal latching surface 278' and the portal sleeve flange 232 rides over latch 276 to be latched in the retracted position with the flange 232 being locked against proximal latching surface 278.

With the safety penetrating instrument 220 in the locked retracted position illustrated in FIG. 7, the distal end of the portal sleeve will be disposed proximally of the distal end of the safety shield a distance X. Safety shield distal end 244 is aligned with or disposed adjacent to the transverse dimensional transition 294 of the penetrating member. The portal sleeve is locked against movement relative to the penetrating member so only the safety shield is able to move between forward and rear rail member walls. Penetration of a cavity wall is commenced, and the force from tissue contact on the distal end 244 of the safety shield 240 will cause the safety shield to move proximally against the bias of bias member 256 causing flange 244 to move past trigger leg 288' without causing movement of latch 276'; and, accordingly, flange 244 is then positioned proximally of trigger leg 288'. At the same time, radial protrusion 247 carried by the safety shield moves proximally past trigger leg 288 without causing movement of latch 276 since there is no contact of trigger leg 286 with arm extension 280.

Upon entry into the anatomical cavity, the counter force on the distal end 244 of the safety shield will be reduced allowing bias member 256 to move the safety shield distally causing flange 244 to engage trigger leg 288' and protrusion 247 to engage trigger leg 288. Triggers 282 and 282' are thus pivoted counterclockwise looking at FIG. 7 causing legs 286 and 286' to engage arm extensions 280 and 280', respectively. The engagement of legs 286 and 286' with the arm extensions causes the arms to move towards their respective bases moving the latches out of engagement with the rail member forward wall and the portal sleeve flange thereby allowing springs 258 and 258' to move the safety shield and portal sleeve distally to their extended protruding positions wherein the portal sleeve and safety shield distal ends protrude beyond the distal end of the penetrating member as shown in FIG. 8. The penetrating unit 224 including the penetrating member 238 and the safety shield 240 can then be withdrawn from the portal unit 222 leaving the portal sleeve 226 in place.

From the above, it will be appreciated that the safety shield or probe of the safety penetrating instrument of the present invention is movable proximally against a distal bias during penetration of an anatomical cavity wall and will thus be moved distally upon entering the anatomical cavity thereby triggering release of a locking mechanism holding the cannula, the safety shield or probe, or both the cannula and the safety shield or probe in retracted positions relative to the distal end of the penetrating member. Once released, the cannula and/or safety shield or probe are moved to extended protruding positions to function as safety members protecting the distal end of the penetrating member. By "safety member" is meant any structure movable relative to the penetrating member to protect the tip of the penetrating member within an anatomical cavity. Since in the safety penetrating instrument of the present invention one or both of a cannula and a safety shield or probe can be extended to protect the penetrating member tip, each can function as a "safety member" upon penetration of the safety penetrating instrument into an anatomical cavity. The cannula, whether or not it functions as a safety member, can be a portal sleeve, a needle open at both ends with fluid flow therethrough, a catheter or any other tubular component of a medical instrument. When the cannula is not triggered to protrude as a safety member, it is coupled with a safety member such as a tubular safety shield disposed between the cannula and penetrating member, a safety probe fitted within a hollow penetrating member, or a component partly within and around the penetrating member and movable to protrude relative to the penetrating member to protect the distal end thereof when triggered. On the other hand, if the cannula does function as a safety member, it can be coupled with a standard safety shield that is not triggered to protrude or with any of the aforementioned safety members. Redundant safety can also be achieved by biasing the cannula and/or penetrating member distally while allowing one or both to move proximally during penetration and triggering release of the safety member in response to distal movement of one or more of the cannula, the safety shield or probe and the penetrating member upon entry into the anatomical cavity. Additionally, the triggered safety member protrusion can be combined with penetrating member retraction to provide separate modes of safety.

In the embodiments shown, either the distal end of the cannula or the distal end of the safety shield is aligned with a transverse dimensional transition in the penetrating member at the penetrating member distal end immediately prior to use in penetrating the anatomical cavity wall; and since the safety shield is movable during penetration, the distal end of the safety shield becomes displaced proximally from its original position relative to the penetrating member during penetration, triggering safety member protrusion when moving distally toward the original position upon entering the anatomical cavity.

FIG. 9 shows an alternative distal configuration for the safety penetrating instruments of the present invention wherein the distal end 30 of the portal sleeve or cannula 26 is located proximally of the penetrating member distal end transition 94 prior to being used for penetrating an anatomical cavity wall and the safety shield distal end 44 is positioned intermediate the distal end transition 94 and the portal sleeve distal end 30. In this configuration the safety shield distal end 44 will begin to move further proximally towards aligning with the portal sleeve distal end 30 after the penetrating member has penetrated the anatomical cavity wall to a predetermined depth X, and the safety shield 40 will spring back towards its original position proximal of the penetrating member distal end upon entering into the anatomical cavity thereby triggering release of the portal sleeve, the safety shield or both members to move distally beyond the penetrating member distal end to function as safety members. In order that the safety shield and portal sleeve distal ends may align during penetration to present a smooth penetrating profile, the distance Y separating the distal ends prior to penetration should approximately equal the distance between rail member forward and rearward walls.

Depending on the initial spacing between the safety shield and portal sleeve distal end, the safety shield may move into alignment with and stop next to the distal end of the safety shield portal sleeve, not reach the distal end of the portal sleeve, or reach the distal end of the portal sleeve and continue to move proximally relative to the portal sleeve during penetration.

The components of the safety penetrating instrument of the present invention can be made of any suitable, medical grade materials to permit sterilization for re-use or for single patient use. The components can be made of multiple parts of various configurations and materials to reduce cost. The portal unit can have various valves, stop cocks and seals in the housing to control fluid flow therethrough, and conventional detent mechanisms can be used to connect or latch the hub with the housing when the portal unit and the penetrating unit are assembled. The distal ends of the cannula and the safety shield can be chamfered or blunt, smooth or roughened, or have any other configuration depending on the need for ease of penetration or increased resistance; and when a safety shield is provided it can be mounted either by the portal unit or the penetrating unit depending on the desirability of being left in place or withdrawn with the penetrating member.

Figure 10:
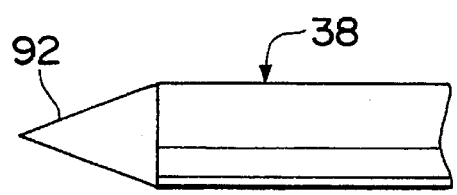
FIGS. 10–15 are side views of alternative distal configurations for the penetrating member of the safety penetrating instrument of the present invention.
Figure 11:
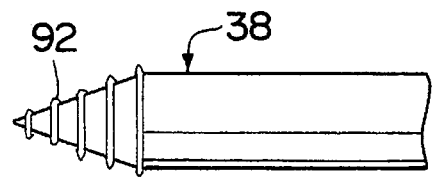
Figure 12:
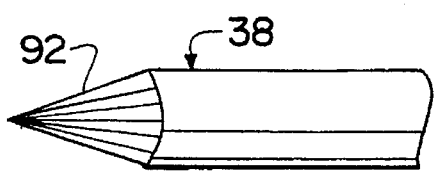
Figure 13:
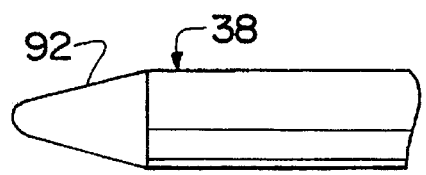
Figure 14:
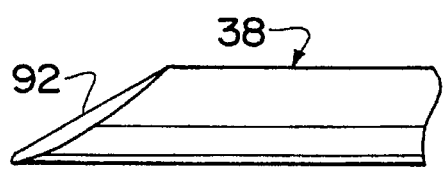
Figure 15:
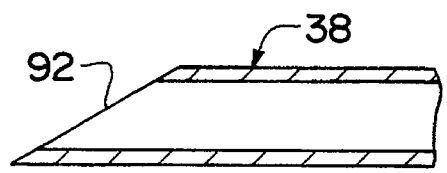

The penetrating member can be solid, hollow or partially solid and hollow, formed as single or multiple pieces, and fixed as shown or movable telescopically over a guide tube or the like. The distal end 92 of the penetrating member 38 can have any configuration desired for a particular procedure, for example, the pyramidal trocar configuration shown or a conical distal end (FIG. 10), a threaded distal end (FIG. 11), a multifaceted distal end (i.e., having two or more facets as shown in FIG. 12), a blunt distal end (FIG. 13), a slanted distal end (FIG. 14) or a hollow needle configuration with fluid flow therethrough (FIG. 15). Additionally, the surface defining the distal end of the penetrating member can be irregular or smooth, continuous or perforated, provided with cutting features or having any combination of the above. If the penetrating member is a hollow needle having a beveled distal end 92 as shown in FIG. 15 or a curved Tuohey-type distal configuration, the proximal edge of the opening at the distal end 92 of the needle is considered the transverse dimensional transition 94 and thus the cannula and/or safety shield distal end is aligned with the distal end of the needle when located adjacent the proximal edge.

Figure 16:
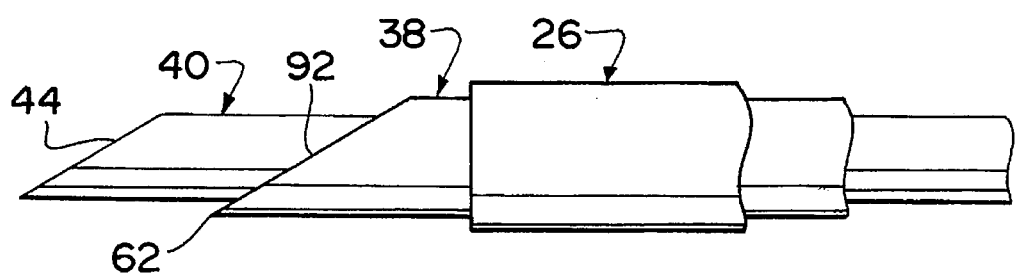
FIG. 16 is a side view, partly in section, of the distal end of a penetrating member configured to accommodate a safety probe.

As mentioned previously, the safety member of the present invention can be a tubular member such as the cannula or a safety shield disposed between the cannula and penetrating member, or in the case of a hollow penetrating member, the safety member can be a probe disposed at least partially within the penetrating member and movable through one or more apertures formed at or near the distal end of the penetrating member. FIG. 16 shows a cannula 26 surrounding a hollow penetrating member 38 with a beveled distal opening and a cylindrical safety probe 40 in an extended protruding position to protect the distal end 92 of the penetrating member 38. The safety probe 40 has a beveled distal end 44 and is preferably movable from the extended position shown to a retracted position where the beveled distal end of the safety probe is flush with the distal end of the penetrating member. It will be appreciated that a coaxial extending mechanism can be fitted within the penetrating member to move the safety probe to the extended position or a flange can be carried at the safety probe proximal end and passed through a slot or opening in the penetrating member to be acted on by any of the extending mechanisms previously described. Also, the safety probe distal end can have any configuration to protrude through single or multiple openings formed in the penetrating member distal end and can conform to the distal profile of the penetrating member or present a discontinuous surface.

The rail member can have various configurations to engage the latch and be released by the trigger. Preferably, the rail member will have a configuration to serve as a stop or abutment for the operating member (i.e., the safety shield flange) as exemplified herein by a U-shaped rail member.

The locking and releasing mechanisms require only a latch for locking the safety member in the retracted position and a trigger for releasing the latch in response to distal movement of the operating member; and, thus, it will be appreciated that various mechanisms can be employed to produce the locking and releasing functions such as, for example, multiple movably or pivotally mounted cams or pawls. It will be appreciated that the locking and releasing mechanism can be designed and arranged in the housing or the hub in various ways to minimize the length of the housing or the hub and, therefore, the overall length of the housing and hub. Various locking and releasing mechanisms that can be simply modified for use in the safety penetrating instrument of the present invention are disclosed in applicant's pending applications Ser. No. 07/800,507, filed Nov. 27, 1991, Ser. No. 07/805,506, filed Dec. 6, 1991, Ser. No. 07/808,325, filed Dec. 16, 1991, Ser. No. 07/848,838, filed Mar. 10, 1992, Ser. No. 07/868,566 and Ser. No. 07/868,578, filed Apr. 15, 1992, Ser. No. 07/929,338, filed Aug. 14, 1992, Ser. No. 07/845,177, filed Sep. 15, 1992, Ser. No. 07,945, 177, filed Sep. 15, 1992, Ser. No. 08/079,586, filed Jun. 22, 1993, Ser. No. 08/195,512, filed Feb. 14, 1994, Ser. No. 08/196,029, filed Feb. 14, 1994, Ser. No. 08/196,027, filed Feb. 14, 1994, Ser. No. 08/195,178, filed Feb. 14, 1994, Ser. No. 08/237,734, filed May 4, 1994, Ser. No. 08/247,205, filed May 20, 1994, Ser. No. 08/254,007, filed Jun. 3, 1994 and Ser. No. 08/260,439, filed Jun. 15, 1994, the disclosures of which are incorporated herein by reference. The above applications disclose automatically retracting safety penetrating instruments such that modification of the locking and releasing mechanisms requires configuring the latches to lock a member in a retracted position rather than in an extended position. The above applications also disclose various bias arrangements useful with the safety penetrating instrument of the present invention. Other locking and releasing mechanisms that can be used in the safety penetrating instrument of the present invention are disclosed in applicant's copending patent applications Ser. Nos. 08/279,170 and 08/279,172, filed Jul. 22, 1994, the disclosures of which are incorporated herein by reference.

One or more control buttons, such as that described in Applicant's copending patent application, Ser. No. 08/083,220, filed Jun. 24, 1993, the disclosure of which is incorporated herein by reference, can be mounted next to any latch for manually disengaging the latch to prevent locking of the safety member in the retracted position, thereby converting the safety penetrating instrument to a standard safety shielded penetrating instrument without triggered protrusion. In addition, any latch can carry a secondary pawl or protrusion at a distal end for locking the safety member in the extended position and can then be released through the use of a control button as described above.

It will also be appreciated that the safety penetrating instrument of the present invention permits use of strong bias springs to ensure movement of the safety member (whether it be a cannula, a safety shield or probe, or both) to the extended protruding position without increasing the force to penetrate. After penetration of the safety penetrating instrument into the anatomical cavity, the safety member acts as a shock absorber upon inadvertent contact with tissue which contact can be felt by the surgeon and visually determined by movement of the handle. The distal bias for the safety shield or probe of the safety penetrating instrument need only be strong enough to allow slight movement of the safety shield or probe during penetration such that the force-to-penetrate can be minimized. The features of the various embodiments described above can be combined in any manner desired dependent upon the requirements and complexity of the safety penetrating instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A safety penetrating instrument for establishing a portal in the wall of an anatomical cavity comprising a housing;

an elongate cannula mounted by said housing and having a distal end for introduction in the anatomical cavity and a proximal end for positioning externally of the anatomical cavity;

a penetrating member disposed in said cannula and fixed relative to said housing, said penetrating member having a distal end for penetrating the anatomical cavity wall;

a safety member disposed within said cannula and having a distal end, said safety member being movable relative to said housing between an extended position where said safety member distal end protrudes distally from said penetrating member distal end and a retracted position where said safety member distal end is disposed proximally of said penetrating member distal end to expose said penetrating member distal end;

extending means for moving said safety member distally relative to said housing from said retracted position to said extended position;

means for manually moving said safety member proximally relative to said housing from said extended position to said retracted position;

locking means for locking said safety member in said retracted position to prevent distal movement of said safety member relative to said housing from said retracted position to said extended position while permitting proximal movement of said safety member relative to said housing from said retracted position during penetration of the anatomical cavity wall;

bias means for biasing said safety member distally relative to said housing in said retracted position while permitting proximal movement of said safety member relative to said housing from said retracted position during penetration of the anatomical cavity wall and distally relative to said penetrating member upon introduction in the anatomical cavity; and releasing means responsive to movement of said safety member distally upon introduction in the anatomical cavity for triggering release of said locking means to permit said extending means to move said safety member distally relative to said housing from said retracted position to said extended position.

2. A safety penetrating instrument as recited in claim 1 wherein said safety member is a safety shield disposed between said penetrating member and said cannula.

3. A safety penetrating instrument as recited in claim 1 wherein said safety member is a safety probe disposed within said penetrating member.

4. A safety penetrating instrument as recited in claim 1 wherein said safety member distal end is distally spaced from said cannula distal end when said safety member is in said retracted position.

5. A safety penetrating instrument as recited in claim 4 wherein said penetrating member distal end extends distally from a transverse dimensional transition in said penetrating member and said safety member distal end is aligned with said transition when in said retracted position.

6. A safety penetrating instrument as recited in claim 4 wherein said penetrating member distal end extends distally from a transverse dimensional transition in said penetrating member and said safety member distal end is located proximally of said transition when in said retracted position.

7. A safety penetrating instrument as recited in claim 4 wherein said penetrating member distal end extends distally from a transverse dimensional transition in said penetrating member and said safety member distal end is located distally of said transition when in said retracted position.

8. A safety penetrating instrument for establishing a portal in the wall of an anatomical cavity comprising a housing;

an elongate cannula mounted by said housing and having a distal end for introduction in the anatomical cavity and a proximal end for positioning externally of the anatomical cavity;

a penetrating member disposed in said cannula and fixed relative to said housing, said penetrating member having a distal end for penetrating the anatomical cavity wall;

a safety member disposed within said cannula and having a distal end, said safety member being movable relative to said housing between a safety member extended position and a safety member retracted position;

extending means for moving said cannula distally relative to said housing from a cannula retracted position where said cannula distal end is disposed proximally of said penetrating member distal end to a cannula extended position where said cannula distal end protrudes distally from said penetrating member distal end;

means for manually moving said cannula proximally relative to said housing from said cannula extended position to said cannula retracted position;

locking means for locking said cannula in said cannula retracted position to prevent movement of said cannula relative to said housing during penetration;

bias means for biasing said safety member distally relative to said housing toward said safety member extended position while permitting said safety member to move proximally relative to said housing during penetration of the anatomical cavity wall and distally relative to said housing upon introduction in the anatomical cavity; and releasing means responsive to movement of said safety member distally upon introduction in the anatomical cavity for triggering release of said locking means to permit said extending means to move said cannula distally relative to said housing from said cannula retracted position to said cannula extended position.

9. A safety penetrating instrument as recited in claim 8 wherein said safety member is a safety shield disposed between said penetrating member and said cannula.

10. A safety penetrating instrument as recited in claim 8 wherein said safety member is a safety probe disposed within said penetrating member.

11. A safety penetrating instrument as recited in claim 8 wherein said safety member distal end is distally spaced from said cannula distal end when said cannula is in said cannula retracted position and said safety member is in said safety member extended position.

12. A safety penetrating instrument as recited in claim 11 wherein said penetrating member distal end extends distally from a transverse dimensional transition in said penetrating member and said safety member distal end is aligned with said transition when said safety member is in said safety member extended position.

13. A safety penetrating instrument as recited in claim 12 wherein said cannula distal end is in alignment with said safety member distal end when said safety member and said cannula are in said respective safety member and cannula retracted positions.

14. A safety penetrating instrument as recited in claim 11 wherein said penetrating member distal end extends distally from a transverse dimensional transition in said penetrating member and said safety member distal end is located proximally of said transition when said safety member is in said safety member extended position.

15. A safety penetrating instrument as recited in claim 14 wherein said cannula distal end is in alignment with said safety member distal end when said safety member and said cannula are in said respective safety member and cannula retracted positions.

16. A safety penetrating instrument as recited in claim 11 wherein said penetrating member distal end extends distally from a transverse dimensional transition in said penetrating member and said safety member distal end is distally spaced from said transition when said safety member is in said safety member extended position.

17. A safety penetrating instrument as recited in claim 16 wherein said cannula distal end is in alignment with said safety member distal end when said safety member and said cannula are in said respective safety member and cannula retracted positions.

18. A safety penetrating instrument for establishing a portal in the wall of an anatomical cavity wall comprising a housing;

an elongate cannula mounted by said housing and having a distal end for positioning in the anatomical cavity and a proximal end for positioning externally of the anatomical cavity;

a penetrating member disposed in said cannula and fixed relative to said housing, said penetrating member having a distal end for penetrating the anatomical cavity wall;

cannula extending means for moving said cannula distally relative to said housing from a cannula retracted position where said cannula distal end is disposed proximally of said penetrating member distal end to a cannula extended position where said cannula distal end protrudes distally from said penetrating member distal end;

means for manually moving said cannula proximally relative to said housing from said cannula extended position to said cannula retracted position;

cannula locking means for locking said cannula in said cannula retracted position to prevent movement of said cannula relative to said housing during penetration of the anatomical cavity wall;

a safety member disposed within said cannula and having a distal end, said safety member being movable relative to said housing between a safety member extended position where said safety member distal end protrudes distally from said penetrating member distal end and a safety member retracted position where said safety member distal end is disposed proximally of said penetrating member distal end to expose said penetrating member distal end;

safety member extending means for moving said safety member distally relative to said housing from said safety member retracted position to said safety member extended position;

means for manually moving said safety member proximally relative to said housing from said safety member extended position to said safety member retracted position;

safety member locking means for locking said safety member in said safety member retracted position to prevent distal movement of said safety member relative to said housing from said safety member retracted position to said safety member extended position while permitting proximal movement of said safety member relative to said housing from said retracted position during penetration of the anatomical cavity wall;

bias means for biasing said safety member distally relative to said housing in said safety member retracted position while permitting said safety member to move proximally relative to said housing from said safety member retracted position during penetration of the anatomical cavity wall and distally toward said safety member retracted position upon introduction in the anatomical cavity; and releasing means responsive to movement of said safety member distally upon introduction in the anatomical cavity for triggering release of said cannula and safety member locking means to permit said cannula and safety member extending means to move said cannula and safety member distally relative to said housing from their respective retracted positions to their respective extended positions.

19. A safety penetrating instrument as recited in claim 18 wherein said safety member includes a safety shield disposed between said cannula and said penetrating member.

20. A safety penetrating instrument as recited in claim 18 wherein said safety member includes a safety probe disposed within said penetrating member.

21. A safety penetrating instrument as recited in claim 18 wherein said cannula distal end is spaced proximally from said safety member distal end when said cannula is in said cannula retracted position and said safety member is in said safety member extended position.

22. A safety penetrating instrument as recited in claim 21 wherein said penetrating member distal end extends distally from a transverse dimensional transition in said penetrating member and said safety member distal end is aligned with said transition when said safety member is in said extended position.

23. A safety penetrating instrument as recited in claim 22 wherein said cannula distal end is in alignment with said safety member distal end when said safety member and said cannula are in said respective safety member and cannula retracted positions.

24. A safety penetrating instrument as recited in claim 21 wherein said penetrating member distal end extends distally from a transverse dimensional transition in said penetrating member and said safety member distal end is located proximally of said transition when said safety member is in said safety member extended position.

25. A safety penetrating instrument as recited in claim 24 wherein said cannula distal end is in alignment with said safety member distal end when said safety member and said cannula are in said respective safety member and cannula retracted positions.

26. A safety penetrating instrument as recited in claim 21 wherein said penetrating member distal end extends distally from a transverse dimensional transition in said penetrating member and said safety member distal end is distally spaced from said transition when said safety member is in said safety member extended position.

27. A safety penetrating instrument as recited in claim 26 wherein said cannula distal end is in alignment with said safety member distal end when said safety member and said cannula are in said respective safety member and cannula retracted positions.

* * * * *